United States Patent [19]
Schneider

[11] Patent Number: 5,250,064
[45] Date of Patent: Oct. 5, 1993

[54] SHIELD FOR SURGICAL SCALPEL BLADES

[75] Inventor: Aaron Schneider, St. Petersburg, Fla.

[73] Assignee: Biological Tissue Reserve, Inc., St. Petersburg, Fla.

[21] Appl. No.: 957,221

[22] Filed: Oct. 7, 1992

[51] Int. Cl.$^5$ ............................................. A61B 17/32
[52] U.S. Cl. .................... 606/167; 606/172; 30/151
[58] Field of Search ................ 30/51, 151, 155, 162, 30/55, 153, 156; 606/167, 170, 172, 181, 182

[56] References Cited

U.S. PATENT DOCUMENTS

| | | | |
|---|---|---|---|
| 529,212 | 2/1866 | Whittemore | 606/182 |
| 628,259 | 7/1899 | Wheeler | 30/162 |
| 2,735,176 | 2/1956 | Costin | 30/162 |
| 3,879,847 | 4/1975 | Roll | 30/162 |
| 4,091,537 | 5/1978 | Stevenson, Jr. | 30/151 |
| 4,523,379 | 6/1985 | Osterhout et al. | 30/151 |
| 4,980,977 | 1/1991 | Motin et al. | 30/151 |

FOREIGN PATENT DOCUMENTS 3722899  1/1989  Fed. Rep. of Germany ...... 606/167

*Primary Examiner*—John D. Yasko
*Assistant Examiner*—N. Kent Gring
*Attorney, Agent, or Firm*—Walter J. Monacelli

[57] ABSTRACT

The surgical instrument guard described herein comprises a shield which fits over the blade of a scalpel and prevents accidental contact or "sticks" with the blade when not in surgical use. In one modification pressure of the surgeon's thumb or finger lifts the shield away from the blade so that the blade may be used in surgery. When the pressure is released, the shield returns to its protective position. In another modification the position of the blade is controlled by a peg or short bar extending into a slot in the side of a protective shield. The shield may be moved forward or backward as far as the slot can move with respect to the peg. When the shield is in the forward position, the shield covers the blade and protects against accidental "sticks". When the shield is moved backward, the blade is exposed and is available for surgical use.

3 Claims, 1 Drawing Sheet

SHIELD FOR SURGICAL SCALPEL BLADES

BACKGROUND OF THE INVENTION

1. Field of the Invention

This invention relates to a device for guarding against accidental stab wounds or cuts from a surgical instrument such as a scalpel. More specifically it relates to a scalpel having an attachment which covers the scalpel blade while the scalpel is not in use. Still more specifically it relates to such a scalpel attachment which may be easily retracted or moved away from the scalpel blade when it is time for the scalpel to be used on a patient. Still more specifically it relates to one such attachment which effects movement of the "guard" away from the scalpel blade by pressure applied by the thumb or finger of the surgeon while the scalpel is being used.

2. State of the Prior Art

Aids and related diseases are the scourge of the 20th century as was syphilis in medieval times such infections occur when there is cross contamination of body fluids. In a surgical setting this cross contamination occurs when fluid of one individual's body is introduced or "inoculated" into another person. Masks with eye shields are already in use in modern surgical suits to prevent blood splashing into the eyes of surgeons and operating crews.

As a virus, Aids and Hepatitis organisms to survive must be sheltered in warm tissues or fluids. Transmission is therefore unlikely to occur with casual skin contact, but if a contaminated needle or blade pierces the skin, an inoculation of viable virus organism is probable, and may result in incurable diease and eventually death. Unfortunately, the number of Aids-affected patients is increasing rapidly and many of these people will require surgical procedures.

Inoculation occurs when a foreign material is introduced accidentally or on purpose to a new area or medium. For present purposes the discussion is limited to undesirable accidental "sticks" caused by contaminated needles or blades.

Routinely the surgical technician opens blades and needles. Accidental needle "sticks" are of little consequence at this stage since a needle can simply be discarded. Obviously, if not, the patient can be inoculated with the technician's fluids.

From a practical standpoint, most accidental "sticks" occur after the intended use of the instrument is complete when attention is directed elsewhere and a sharp edge or needle is picked up with other instruments or bumped (i.e., such as in clearing surgical trays). This results in patient to physician or staff inoculation.

Accidental "sticks" occur all too frequently in the hospital setting. In a brief canvas by the author many technicians admitted one to five "sticks" per month. In addition as a point of interest blood banks will not accept a donor's blood for twelve months following a "stick".

Accidental needle "sticks" and minor "stab wounds" from sharp surgical instruments in the operating rooms of hospitals continue at an unacceptable rate. To this inventor's knowledge an efficient intraoperative protective device has never been used. Instead operating room technicians and surgeons are taught "Proper Technique" and "Universal Safety Standards". These methods help prevent "sticks" but do not stop accidents from occurring. A completely guarded blade or needle will not cause an accident.

Receiving a guarded instrument that is exposed only during use (i.e., cutting) would assure maximum protection against accidental injury when handed back to the technician. If the scalpel is dropped or mishandled, the blade may be immediately covered by spring action of the shield.

OBJECTIVES

It is an object of this invention to have a simple device for guarding against accidental "sticking" by sharp surgical instruments, such as scalpels, etc.

It is also an object of this invention to have a guard or shield for a scalpel blade capable of being easily repositioned as to expose the blade for surgical use.

It is also an object of this invention to have the scalpel shield easily retractable by pressure from the surgeon's thumb or finger while the scalpel is being used in surgery.

It is also an object of this invention to have the scalper blade exposed for surgical use.

Other objects will become obvious upon reading the details of this invention as described below.

STATEMENT OF THE INVENTION

In accordance with the present invention it has been found that the above objectives are fully met by the operation of the improved device of this invention. This device comprises a shield or guard which covers and protects the blade of a scalpel when it is not in use but is easily shifted out of protective position when the scalpel is needed for surgery. In one preferred modification the shield may be lifted away from the protective position by the application of pressure by the surgeon's thumb or finger.

In the first of these preferred modifications a clip is adapted to fit tightly over and at least partially embrace the scalpel handle and a shield is adapted to fit over at least a portion of this clip and extend beyond the length and width of the blade of the scalpel. This shield has the end thereof which extends over the scalpel handle raised at an angle to the portion of the shield which extends over the scalpel blade. The shield is pivotally connected to this clip so that when downward pressure is applied to this angular portion of the shield, the opposite end of the shield will be raised away from the blade, whereby the blade is freed for surgical use. The pivoting means is preferably a peg or short bar extending outward from one side or preferably both sides of the clip. These pegs are adapted to fit into openings in the shield so that they will serve as fulcrum points when downward pressure is applied on the angular portion of the shield thereby causing the desired pivoting. When the pressure is released from this angular portion of the shield, the opposite portion of the shield returns to its protective position over the scalpel blade. This return to protective position is effected by a spring means which applies upward pressure between this angular portion of the shield and the clip.

SPECIFIC EMBODIMENT OF THE INVENTION

The device of this invention may be further described by reference to the drawings in which.

Figure 1:
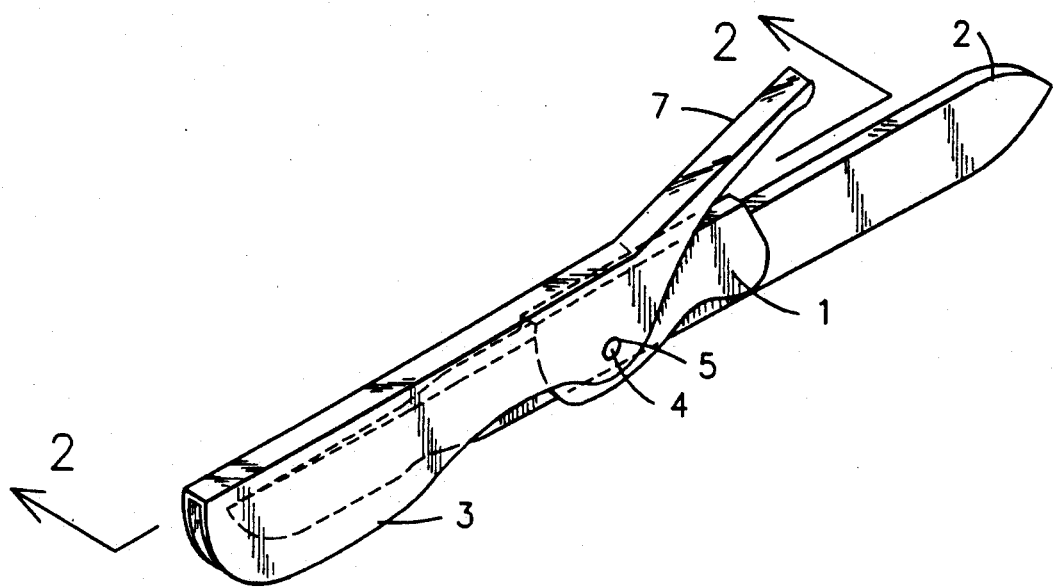
FIG. 1 is a perspective view of a preferred modification of this invention.
Figure 2:
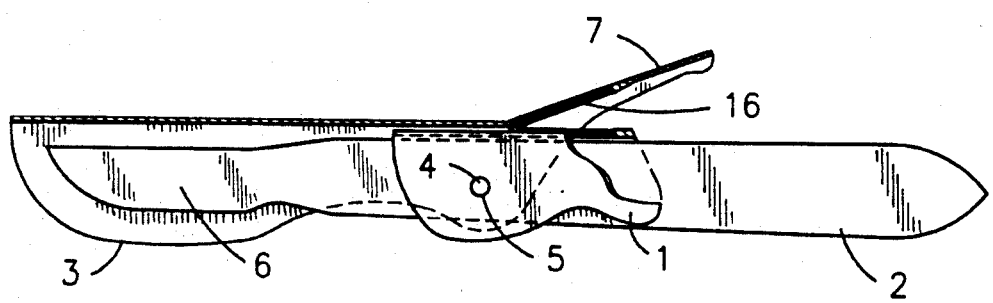
FIG. 2 is a side elevational view of the modification of FIG. 1 with a cross-sectional view taken at line 2—2 of FIG. 1.
Figure 3:
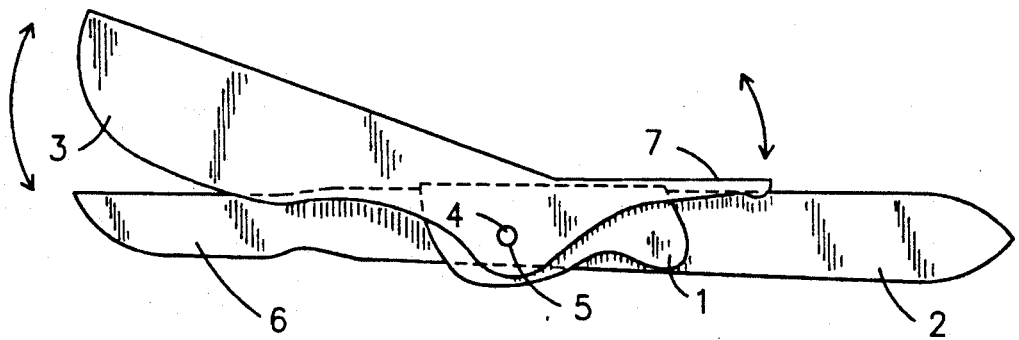
FIG. 3 is side elevational view of the modification of FIG. 1 with the blade of the scalpel shown exposed.

In the modification of FIGS. 1-3, clip 1 is fitted tightly onto scalpel handle 2. Shield 3 is pivotally attached to clip 1 by means of pin 4 which fits into an opening 5 in shield 3. Blade 6 is covered by shield 3. The end portion 7 of shield 3 is angled upward. When downward pressure is applied to end portion 7, the opposite end of shield 3 is raised so as to expose blade 6 thereby allowing it to be freed for surgical use. When this pressure is released, the shield returns to the position shown in FIGS. 1 and 2 whereby accidental sticks or cuts are prevented. This return is effected by V-shaped spring 16 which is retained by one recess in the upper part of clip 1 and by another recess in end portion 7.

The shield and clip may be removed after use of the scalpel for surgery and the shield clip and scalpel may be sterilized for subsequent re-use. The usual methods for sterilization may be used such as autoclaving to a temperature of 270° F. for 20 minutes and 15 pounds per square inch, gas sterilization, or gamma radiation.

While certain features of this invention have been described in detail with respect to various embodiments thereof, it will of course be apparent that other modifications can be made within the spirit and scope of this invention, and it is not intended to limit the invention to the exact details insofar as they are defined in the following claims.

The invention claimed is:

1. A guarding device, adapted to be fitted onto a scalpel having a handle and a sharp blade extending from said handle, said device comprising:
   (a) a clip which is adapted to fit tightly over and to at least partially embrace the handle of a scalpel when said scalpel is inserted into said clip;
   (b) a shield adapted to fit over at least a portion of said clip, said shield having a first end adapted to extend beyond said blade, a main body portion adapted to cover said blade and a second end which extends upward at an angle to said main body portion;
   (c) a pivoting means positioned below the point where said second end of said shield angles upward from said main body portion, said pivoting means being capable of pivoting said first end of said shield on said clip from a first position by pressure applied on said second end upward to a second position, so that when a scalpel is positioned with its handle in said clip, the blade of said scalpel will be exposed when said shield is in said second position, and said blade will be protected when said shield is put in said first position.

2. The device of claim 1 in which there is a spring means by which, upon release of said downward pressure on said second end the shield is returned to its first position.

3. The device of claim 2 in which said spring means comprises a flat first plate and a second flat plate, said plates being joined together at one end of each plate and the other end of each plate being spaced from each other so when pressure is applied to the unattached ends to bring them together, a spring action is thereby generated.

* * * * *